(12) United States Patent
Mekhail et al.

(10) Patent No.: US 9,480,510 B2
(45) Date of Patent: Nov. 1, 2016

(54) DEVICES, SYSTEMS AND METHODS OF ATTACHING SAME TO THE SPINE

(75) Inventors: Anis Mekhail, Willow Spring, IL (US); Steven E. Mather, Hinsdale, IL (US); Wagdy W. Asaad, Burr Ridge, IL (US); Thibaut Guffroy, Westchester, IL (US)

(73) Assignee: SpineCraft, LLC, Westmont, IL (US)

( * ) Notice: Subject to any disclaimer, the term of this patent is extended or adjusted under 35 U.S.C. 154(b) by 899 days.

(21) Appl. No.: 13/070,242

(22) Filed: Mar. 23, 2011

(65) Prior Publication Data
US 2012/0245641 A1    Sep. 27, 2012

(51) Int. Cl.
*A61B 17/80* (2006.01)
*A61B 17/70* (2006.01)

(52) U.S. Cl.
CPC ....... *A61B 17/8047* (2013.01); *A61B 17/7059* (2013.01); *A61B 17/80* (2013.01); *A61B 17/8033* (2013.01)

(58) Field of Classification Search
CPC .......... A61B 17/8061; A61B 17/8033; A61B 17/7061; A61B 17/70; A61B 17/88; A61B 17/8047; A61B 17/7059
USPC ..................................... 606/70–71, 280–299
See application file for complete search history.

(56) References Cited

U.S. PATENT DOCUMENTS

| | | |
|---|---|---|
| 4,762,122 A | 8/1988 | Slocum |
| 5,439,381 A | 8/1995 | Cohen |
| 5,470,333 A | 11/1995 | Ray |
| 5,501,684 A | 3/1996 | Schlapfer et al. |
| 5,603,713 A | 2/1997 | Aust et al. |
| 5,616,144 A | 4/1997 | Yapp et al. |
| 5,653,763 A | 8/1997 | Errico et al. |
| 5,672,175 A | 9/1997 | Martin |
| 5,681,311 A | 10/1997 | Foley et al. |
| 5,718,705 A | 2/1998 | Sammarco |
| 5,735,853 A | 4/1998 | Olerud |
| 5,749,872 A | 5/1998 | Kyle et al. |
| 5,902,303 A | 5/1999 | Eckhof et al. |
| 5,951,557 A | 9/1999 | Luter |
| 5,954,722 A | 9/1999 | Bono |
| 6,030,389 A | 2/2000 | Wagner et al. |
| 6,123,709 A | 9/2000 | Jones |

(Continued)

FOREIGN PATENT DOCUMENTS

| | | |
|---|---|---|
| CA | 2341305 | 2/2000 |
| FR | 2790198 | 9/2000 |

(Continued)

OTHER PUBLICATIONS

Biomet C-Tek MaxAn, Jul. 2008.

(Continued)

*Primary Examiner* — Anu Ramana
*Assistant Examiner* — Jessica Weiss
(74) *Attorney, Agent, or Firm* — Alan W. Cannon

(57) ABSTRACT

Systems and method for fixation to a spinal column are described. A system includes a plate having an anterior surface, a posterior surface, a longitudinal axis, a transverse axis and a through hole passing through the anterior and posterior surfaces; and a dynamic fixator interface member configured and dimensioned to connect to the plate within the through hole and to axially slide relative to the plate in directions of the longitudinal axis, and additionally, to rotate relative to the plate in directions about the transverse axis.

21 Claims, 6 Drawing Sheets

(56) References Cited

U.S. PATENT DOCUMENTS

| | | | |
|---|---|---|---|
| 6,129,730 A | 10/2000 | Bono et al. | |
| 6,348,052 B1 | 2/2002 | Sammarco | |
| 6,533,786 B1 | 3/2003 | Needham et al. | |
| 6,629,998 B1 | 10/2003 | Lin | |
| 6,663,632 B1 | 12/2003 | Frigg | |
| 6,902,565 B2 | 6/2005 | Berger et al. | |
| 7,001,389 B1 | 2/2006 | Navarro et al. | |
| 7,278,997 B1 | 10/2007 | Mueller et al. | |
| 7,758,620 B2 | 7/2010 | Porcher | |
| 7,766,947 B2 | 8/2010 | Hawkes et al. | |
| 7,887,569 B2 | 2/2011 | Frigg | |
| 7,951,179 B2 | 5/2011 | Matityahu | |
| 7,963,982 B2 | 6/2011 | Kirschman | |
| 8,128,628 B2 | 3/2012 | Freid et al. | |
| 8,236,033 B2 | 8/2012 | Paul | |
| 8,262,659 B2 | 9/2012 | Ryan et al. | |
| 2002/0120273 A1 | 8/2002 | Needham et al. | |
| 2004/0220571 A1 | 11/2004 | Assaker et al. | |
| 2005/0182404 A1 | 8/2005 | Lauryssen et al. | |
| 2005/0187548 A1 | 8/2005 | Butler et al. | |
| 2005/0240185 A1 | 10/2005 | Boomer et al. | |
| 2006/0069389 A1 | 3/2006 | Knopfle | |
| 2006/0122604 A1 | 6/2006 | Gorhan et al. | |
| 2006/0195089 A1 | 8/2006 | LeHuec et al. | |
| 2007/0016205 A1 | 1/2007 | Beutter et al. | |
| 2007/0123879 A1* | 5/2007 | Songer et al. | 606/69 |
| 2007/0123886 A1 | 5/2007 | Meyer et al. | |
| 2007/0162011 A1 | 7/2007 | Leyden et al. | |
| 2007/0162013 A1* | 7/2007 | Jacene | A61B 17/1728 606/288 |
| 2007/0162016 A1 | 7/2007 | Matityahu | |
| 2007/0203492 A1 | 8/2007 | Needham et al. | |
| 2007/0233112 A1 | 10/2007 | Orbay et al. | |
| 2008/0027439 A1 | 1/2008 | Sasing | |
| 2008/0306550 A1* | 12/2008 | Matityahu | 606/290 |
| 2009/0012571 A1* | 1/2009 | Perrow et al. | 606/280 |
| 2009/0024170 A1* | 1/2009 | Kirschman | A61B 17/8052 606/280 |
| 2009/0054930 A1* | 2/2009 | Aflatoon | A61B 17/7059 606/246 |
| 2009/0062862 A1* | 3/2009 | Perrow et al. | 606/280 |
| 2009/0264934 A1 | 10/2009 | Youssef et al. | |
| 2011/0112584 A1 | 5/2011 | Frigg | |
| 2011/0238123 A1 | 9/2011 | Kirschman | |
| 2012/0239147 A1 | 9/2012 | Winkler | |

FOREIGN PATENT DOCUMENTS

| | | |
|---|---|---|
| RU | 2044522 | 9/1995 |
| WO | WO0010474 | 3/2000 |

OTHER PUBLICATIONS

English translation of RU2044522 (Machine translation by Patent Translate (Powered by EPO and Google).
English translation of Abstract of FR2790198.

* cited by examiner

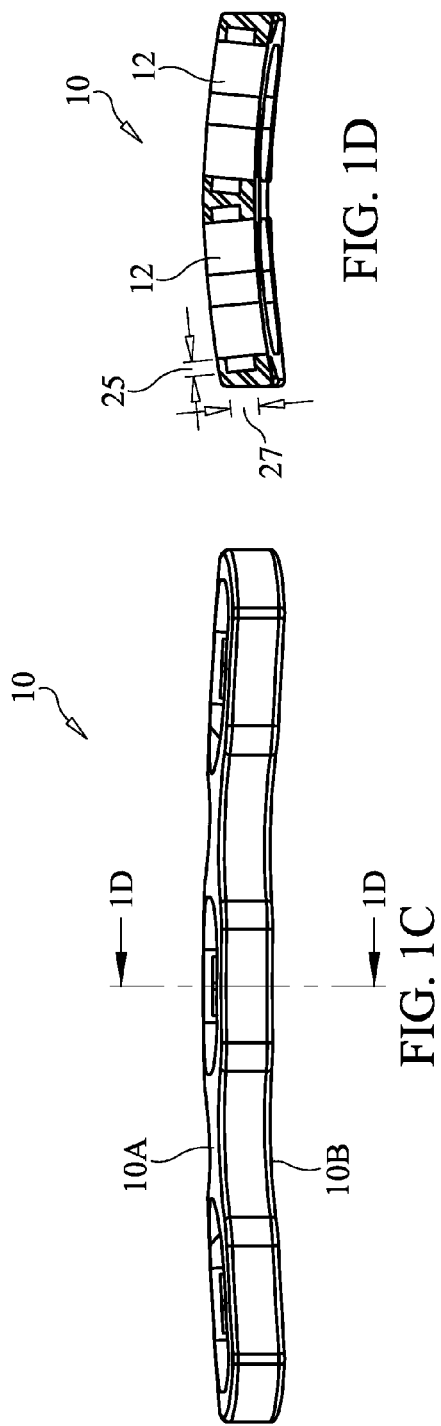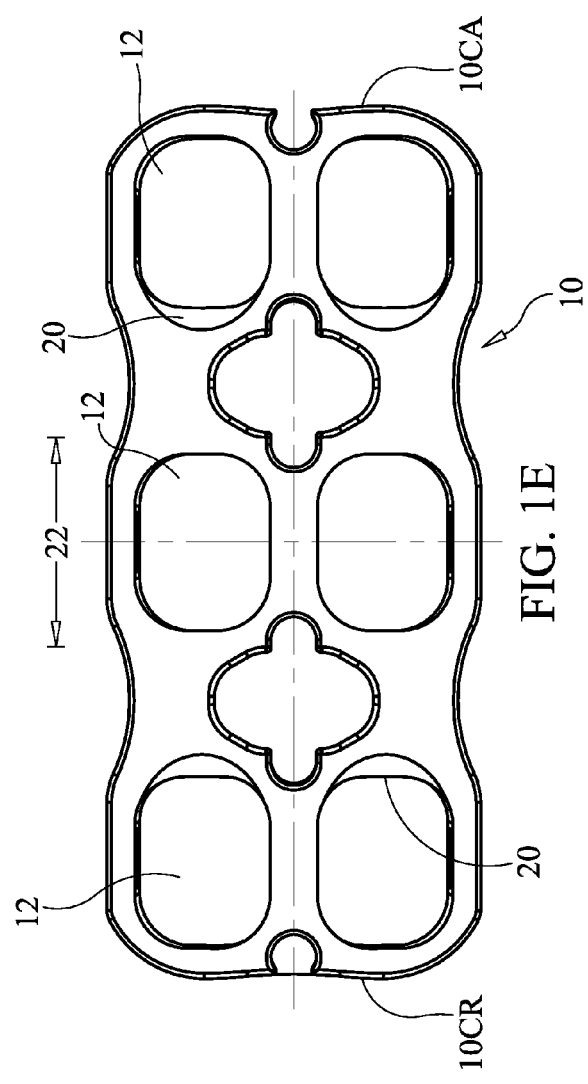

DEVICES, SYSTEMS AND METHODS OF ATTACHING SAME TO THE SPINE

BACKGROUND OF THE INVENTION

Back pain can be caused by a variety of factors, including, but not limited to the rupture or degeneration of one or more intervertebral discs due to degenerative disk disease, spondylolisthesis, deformative disorders, trauma, tumors and the like. In such causes, pain typically results from compression or irritation of spinal nerve roots by reduced spacing between adjacent vertebrae, a damaged disk and/or misalignment of the spine resulting of the injury or degeneration.

Common forms of treating such pain include various types of surgical procedures that include mounting a plate across two or more adjacent vertebrae to stabilize them, including, but not limited to aligning the vertebrae to alleviate pain and achieve bony fusion between said vertebrae. After installation of such a plate, once the patient has recovered to the extent where the patient can at least sit upright, the gravitational forces on the spine typically cause some subsidence forces to be applied to the treated vertebrae, particularly in cases where one or more grafts have been placed between one or more pairs of adjacent vertebrae. Greater amounts of subsidence that what normally occurs (as described above) can result from inadequate grafting technique, poor graft quality and/or poor bone quality (e.g., osteoporosis).

Current plate systems do not provide a screw-plate interface that is adequate to account for the subsidence that occurs. Specifically, current systems do not allow sufficient angulation of the screws relative to the plane of the plate to allow the screws to be oriented as needed during the initial anchoring of the plate to the vertebrae. Further, many current systems do not allow axial movement of the screws relative to the longitudinal axis of the plate to further accommodate subsidence.

There is a continuing need for plates and plate systems that allow improved angulation of screws relative to the face or plane of the plate. There is a continuing need for plates and plates systems that include dynamic features that allow for axial changes in positioning of one or more screws relative to the longitudinal axis or length dimension of the plate that they are installed through, to dynamically accommodate subsidence. The present invention meets at least all of the above needs.

SUMMARY OF THE INVENTION

In one aspect of the present invention, a system for fixation to a spinal column is provided, including: a plate having an anterior surface, a posterior surface, a longitudinal axis, a transverse axis and a through hole passing through the anterior and posterior surfaces; and a dynamic fixator interface member configured and dimensioned to connect to the plate within the through hole and to axially slide relative to the plate in directions of the longitudinal axis, and additionally, to rotate relative to the plate in directions about the transverse axis.

In at least one embodiment, slots are provided in opposite inner walls of the through hole, wherein the dynamic fixator interface member slides in the slots.

In at least one embodiment, the slots are closed-ended, i.e., open at an end opening to the surface of the inner walls and closed at opposite end.

In at least one embodiment, the dynamic fixator interface member comprises a ring-shaped main body and first and second extensions extending from first and second sides of the ring-shaped main body, wherein the first and second extension slide in the slots.

In at least one embodiment, the first and second extensions are configured to rotate in first and second directions in the slot, relative to the transverse axis of the plate.

In at least one embodiment, the first and second extensions each comprise a first end, a second end and an intermediate location, wherein each intermediate location has a first thickness, and each of the first and second ends have a second thickness, the first thickness being greater than the second thickness, and wherein the surfaces of the extensions taper linearly from the intermediate location to the first and second ends, respectively, for each of the first and second extensions.

In at least one embodiment, an angle formed by one of the tapered surfaces relative to a line connecting the first and second ends of one of the first and second extensions is in the range of about twenty-five degrees to about forty-five degrees.

In at least one embodiment, the angle is about thirty degrees.

In at least one embodiment, the dynamic fixator interface member is configured to rotate up to about forty-five degrees relative to the plate in directions about the transverse axis.

In at least one embodiment, the dynamic fixator interface member is configured to rotate not greater than about thirty degrees relative to the plate in directions about the transverse axis.

In at least one embodiment, the dynamic fixator interface member further comprises an anti-backout mechanism configured to prevent backout of a fastener therefrom, once the fastener has been inserted through the dynamic fixator member and fastened to the spinal column, the dynamic fixator member having been located in the through hole.

In at least one embodiment, the dynamic fixator interface member comprises a slotted ring shaped body comprising a slot formed in an end of the body, and the anti-backout mechanism comprises an extension extending from the body.

In at least one embodiment, the system further includes a fastener configured and dimensioned to be received and locked in the dynamic fixator interface member.

In at least one embodiment, the fastener comprises a fixed screw.

In at least one embodiment, the fastener comprises a variable screw.

In another aspect of the present invention, a plate system for fixation to a spinal column is provided, including: a plate having an anterior surface, a posterior surface, a longitudinal axis, a transverse axis and a plurality of through holes passing through the anterior and posterior surfaces; and at least two of the through holes comprising closed-ended slots formed in opposite inner walls of each of the at least two through holes.

In at least one embodiment, a plurality of dynamic fixator interface members are provided, wherein one of the dynamic fixator interface members is received in the slots of each through hole having the slots, respectively, each dynamic fixator interface member being configured and dimensioned to slide in the respective slots of the through hole it is received in, wherein sliding is permitted axially relative to the plate in directions of the longitudinal axis.

In at least one embodiment, each dynamic fixator interface is configured and dimensioned to rotate in the slots, relative to the plate, in directions about the transverse axis.

In at least one embodiment, a plurality of dynamic fixator interface members are provided, wherein one of the dynamic fixator interface members is received in the slots of each the through hole having the slots, respectively, each dynamic fixator interface member being configured and dimensioned to rotate in the respective slots of the through hole it is received in, wherein rotating is permitted relative to the plate in directions about the transverse axis.

In another aspect of the present invention, a plate system for fixation to a spinal column is provided, including: a plate having an anterior surface, a posterior surface, a longitudinal axis, a transverse axis and a plurality of through holes passing through the anterior and posterior surfaces; and a plurality of dynamic fixator interface members, one of each members received in one of each of the through holes, respectively, each dynamic fixator interface member being configured and dimensioned to connect to the plate within the respective through hole and to slide relative to the plate in a plurality of directions, and additionally, to rotate so as to form an angle relative to the anterior surface of the plate.

In another aspect of the present invention, a method of attaching a plate system to the spinal column is provided, including: providing a plate having an anterior surface, a posterior surface, a longitudinal axis, a transverse axis and an upper through hole and a lower through hole, each through hole passing through the anterior and posterior surfaces; a first dynamic fixator interface member connected in the upper through hole and a second dynamic fixator interface member connected in the lower through hole, each dynamic fixator interface member being configured and dimensioned to rotate relative to the plate at an angle to the anterior surface of the plate; and a fastener inserted through each dynamic fixator interface member, respectively; rotating the fastener and dynamic fixator interface member in the upper through hole so that a distal end of the fastener is angled upwardly, relative to the upper through hole and the plate; rotating the fastener and dynamic fixator interface member in the lower through hole so that a distal end of the fastener is angled downwardly, relative to the lower through hole and the plate; fixing the fastener passing though the dynamic fixator interface member in the upper through hole to a first vertebra; and fixing the fastener passing though the dynamic fixator interface member in the lower through hole to a second vertebra below the first vertebra; and wherein the dynamic fixator interface member in the upper through hole and the dynamic fixator interface member in the lower through hole are configured to slide axially in the respective through holes, thereby permitting relative axial movement between the first and second vertebrae via the fasteners, relative to the plate.

In at least one embodiment, the plate is further provided with an additional through hole with an additional dynamic fixator interface member connected in the additional through hole and a fixed fastener is inserted through the additional dynamic fixator interface member, and the method further includes fixing the fixed fastener passing though the additional dynamic fixator interface member in the additional through hole to one of the first vertebra, second vertebra, or an additional vertebra; wherein the fixed fastener is prevented from angulating relative to the additional dynamic fixator and the plate upon performance of the fixing of the fixed fastener.

These and other advantages features of the invention will become apparent to those persons skilled in the art upon reading the details of the systems and methods as more fully described below.

BRIEF DESCRIPTION OF THE DRAWINGS

FIG. 1C shows an end (side) view of the plate of FIG. 1A.

FIG. 1D shows a side section view of the plate of FIG. 1A.

FIG. 1E shows a view of an anterior surface or a surface that faces away from the bone when the plate of FIG. 1A is attached to bone.

DETAILED DESCRIPTION OF THE INVENTION

Figure 1A:
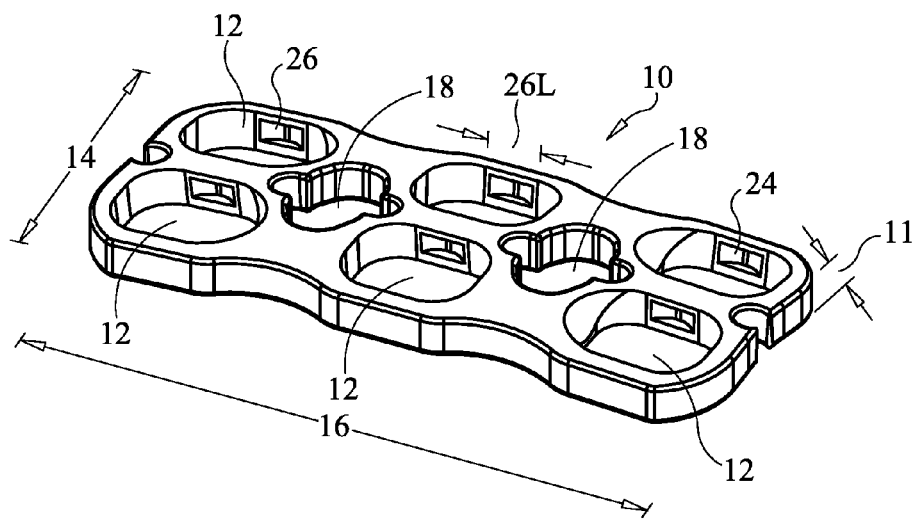
FIG. 1A shows a perspective view of a plate according to an embodiment of the present invention.

Before the present devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a level" includes a plurality of such levels and reference to "the opening" includes reference to one or more openings and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "fixed screw", as used herein, refers to a screw that is designed not to pivot, but rather to be constrained angularly relative to the plate that it interfaces with.

A "variable screw", as used herein, refers to a screw that is designed to pivot (within limits, i.e., to be semi-constrained) relative to the plate that it interfaces with.

Description

Referring now to FIG. 1, a perspective view of a bone plate 10 is shown according to an embodiment of the present invention. Bone plate 10 is configured and dimensioned to be implanted across two adjacent cervical disc spaces, which may or may not retain the natural cervical discs and which may, in either event include one or more implants therein. The embodiment shown in FIG. 1 is thus referred to as a two-level plate 10, as it attaches to two levels of the spine (top portion including top two openings 12 attaches to a first vertebra, middle portion including middle two openings 12 attaches to the next vertebra that is immediately inferior to the first vertebra, and the bottom portion including the bottom two openings 12 attaches to the next vertebra that is immediately inferior to the vertebra that the middle portion is attached to), i.e., traversing two adjacent disc spaces.

Although reference is made to a two-level plate 10 for description of the present invention, it is noted that the present invention is not limited to a two-level plate, but may be provided as a one-level plate, three-level plate, or more, while employing the same dynamic features and screws (although in fewer or greater numbers, depending upon the number of levels spanned) as described herein with respect to a two-level system. Plate 10, whether a two-level plate, a one-level plate or a plate designed to span some other number of levels, is configured and dimensioned to be fixed anteriorly to adjacent cervical vertebrae.

It is further noted that the present invention is not only not limited to two-level plates, but it is also not limited to cervical plates, as larger versions of the plates described may be provided for fixation to thoraco-lumbar vertebrae of the spine. Still further, the invention is not limited to anterior fixation of a plate to the cervical, thoracic or lumbar spine, as plates may be configured to be fixed to the lateral regions of these spinal regions for example.

Plate 10 is typically made of biocompatible titanium or other biocompatible metal or alloy, but may alternatively be made of a rigid biocompatible polymer or polymer composite. Plate 10 is very low profile in thickness 11 (e.g., within a thickness range of about 1.5 mm to about 3.0 mm (typically about 2.2 mm) for use in treatment of the cervical spine) and in medial-lateral width 14 (e.g., about 12 mm to about 20 mm, in at least one embodiment, about 16 mm. The height 16 of plate 10 will typically range from about 24 mm to about 44 mm, typically about 30 mm for a two-level plate 10, from about 8 mm to about 18 mm, typically about 10 mm for a one-level plate 10, and from about 45 mm to about 96 mm for greater than two-level plates, depending upon how many levels are to be spanned, variations in dimensions among patients, etc. For thoraco-lumbar spine applications, including anterior and antero-lateral applications, height will typically range from about 44 mm to about 64 mm, typically about 52 mm for a two-level plate, height generally ranges from about 12 mm to about 22 mm, typically about 16 mm for a one-level plate and height ranges from about 69 mm to about 14 mm for plates designed for more than two levels. Width generally ranges from about 14 mm to about 30 mm in the thoraco-lumbar embodiments and thickness generally ranges from about 2.4 mm to about 4.0 mm in the thoraco-lumbar embodiments.

Other thicknesses 11, widths 14 and lengths/heights 16 of plate 10 may be employed to use in other areas of the body, such as other bones, such as long bones, pelvis, etc. Plate 10 is not typically planar for spinal uses (although it can be, for other uses), but has a curvature along its height direction (as shown in the side view of FIG. 1C) and has a curvature along the width direction (as shown in Fig. cross-sectional view of FIG. 1D). In this way, the surface of the plate 10 that contacts the vertebrae is concave along two axes (longitudinal axis along the height 16 direction and transverse axis along the width 14 direction) to better conform to the anterior surfaces of the vertebrae that it is fixed to.

Figure 1B:
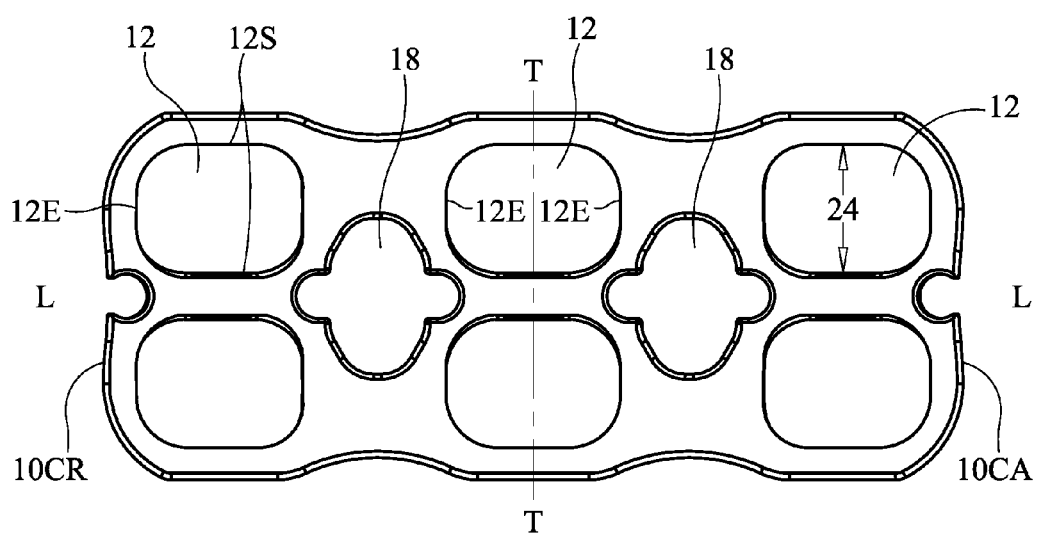
FIG. 1B shows a view of a posterior surface or a surface that contacts the bone when the plate of FIG. 1A is attached to bone.

Plate 10 is further provided with openings 12 and openings 18, as best shown in the bottom view of FIG. 1B. Openings 12 are fixator receptors each configured and dimensioned to receive a dynamic fixator interface member 40 (e.g., see FIG. 2B therein (e.g., see FIG. 3B). Openings 18 allow viewing of the graft or cage inserted between adjacent vertebrae, so that the surgeon can visually confirm that these have been correctly positioned.

FIG. 1E shows an opposite side view of what is shown in FIG. 1B. That is, FIG. 1B shows the surface that contacts the bone when installed as designed, and FIG. 1E shows the opposite surface. Cylindrical cutouts 20 are surface angled at an angle defined to limit the maximum amount of rotation around the rotation axis of the ring (in this example, thirty degrees from a flush orientation of the ring with the plate, although this maximum angulation may be varied during design of the plate 10). It can be seen that the cutouts 20 adjacent the cranial-most openings 12 (pair of openings on left side of FIG. 1E, (i.e., openings 12 closest to cranial end 10CR in FIG. 1E) extend in a direction toward the caudal end 10CA of plate 10. This increases the amount of angulation that a fastener and/or driver can be angled relative to the plate 10, to allow the maximum designed angulation of the distal end of the fastener in the cranial direction. The cutouts 20 adjacent the caudal most openings 12 (i.e., openings 12 closest to caudal end 10CA in FIG. 1E) extend in a direction toward the cranial end 10CR of plate 10. This increases the amount of angulation that a fastener and/or driver can be angled relative to the plate 10, to allow the maximum designed angulation of the distal end of the fastener in the caudal direction. The cutouts 20 adjacent the intermediate openings 12 (pair of openings in the middle in FIG. 1E) do not employ cutouts 20. These arrangements of cutouts, cutout orientations, and lack of cutouts are designed to allow insertion of the screws 70, 70' (or tools) at differing angles through the cranial-most openings 12, intermediate openings 12 and caudal-most openings 12, respectively, e.g. see FIG. 7. Likewise, each of the screws/tools in a pair of screws 70, 70' or tools can be independently angled relative to the other screw or tool in the pair at the same level, as each opening 12 receives a member 40 that is independently rotational and translatable relative to the plate 10 and all other members 40.

The anterior surface 10A or surface of the plate 10 that faces away from the bone when the plate 10 is installed, is convex with a convex curvature along the longitudinal axis L-L direction and a convex curvature along the transverse axis T-T direction, e.g. see FIG. 1B.

The receptacle openings 12 are formed as oblong circles, such that at least portions of opposing sides 12S are parallel to one another, with opposing ends 12E being curved, as shown in the middle two openings 12 of FIG. 1B. The end openings are less curved.

Figure 2A:
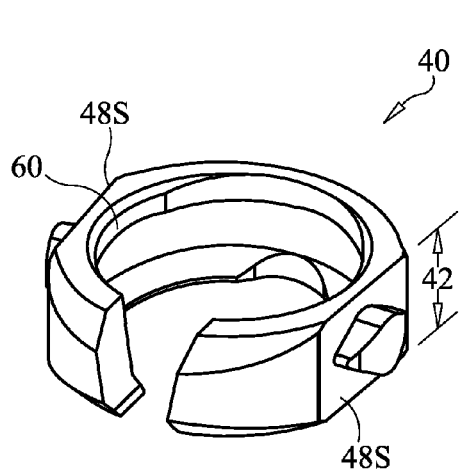
FIG. 2A is a perspective view of a dynamic fixator interface member according to an embodiment of the present invention.
Figure 2B:
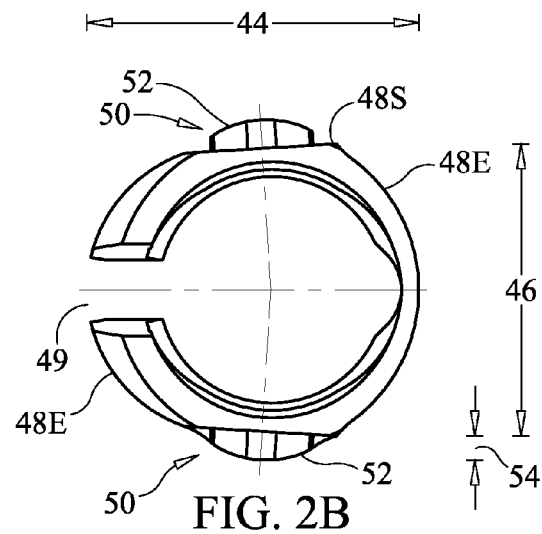
FIG. 2B is a top view of the member of FIG. 2A.
Figure 4:
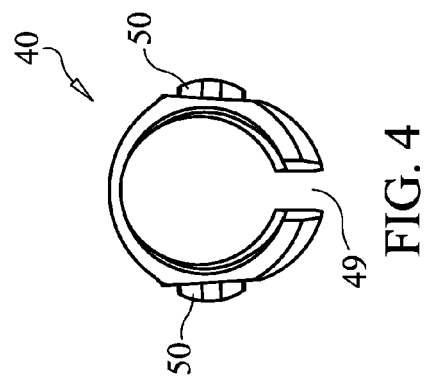
FIG. 4 illustrates a top view of a dynamic member according to an embodiment of the present invention.

FIG. 2A is a perspective view of a dynamic fixator interface member 40 according to an embodiment of the present invention. FIGS. 2B and 4 show top views of the member 40. Member 40 is configured and dimensioned to connect to plate 10 within a receptacle opening 12 thereof. Member 40 is configured with a thickness 42 that is slightly less than thickness 11 of plate 10, e.g., about 0.10 mm to about 0.50 mm thinner, in at least one embodiment configured for the cervical spine, about 0.15 mm thinner, and in at least one other embodiment configured for the cervical spine, about 0.2 mm thinner. For thoraco-lumbar applications, the thickness 42 is slightly less than thickness 11 of plate 10 by a thickness in the range of about 0.15 to about 1.25 mm thinner.

The height/length 44 (see FIG. 2B) of member 40 is less than the height/length 22 (see FIG. 1 E) of the receptacle opening 12 that it is received in. The gap formed between member 40 and the wall forming opening 12 has to be big enough to allow rotation and translation of the member 40 without touching the plate 10/wall defining the opening 12, along the desired range of rotation and translation. The length 44 ranges from about 4.0 mm to about 9.25 mm for cervical applications, and in at least one embodiment, is about 6.665 mm. For thoraco-lumbar applications, the length 44 ranges from about 6.0 mm to about 23.125 mm. The length of 22 ranges from about 5 mm to about 10 mm for cervical applications, and in at least one embodiment is about 7.5 mm. For thoraco-lumbar applications, the length 22 is in the range of from about 7.5 mm to about 25 mm. This, together with further features described below, allows member 40 to slide axially relative to plate 10 in directions along the longitudinal axis L-L.

The width 46 (see FIG. 2B) of the main body 48 of member 40, at its widest portion, is substantially equal to the width 24 (see FIG. 1B) of the receptacle opening 12 that it is received in. The tolerance between the member 40/main body 48 and the wall of the opening should be large enough to allow the member to move freely, but small enough so that the member 40 is maintained in the opening 12 of plate 10. Therefore the dimension of 46 added to twice the dimension of 54 (see FIG. 2B) needs to be greater than the dimension 24 (see FIG. 1B). In at least one cervical embodiment, 46 is about 5.873 mm±about 1 mm and 24 is about 6 mm±about 1 mm, and 54 is about 0.575 mm±about 0.5 mm. In at least one thoraco-lumbar embodiment, 46 is about 8.5 mm±about 2.5 mm and 24 is about 9 mm±about 2.5 mm, and 54 is about 1.0 mm±about 0.5 mm. These arrangements substantially prevent side to side movement (i.e., translation in the direction of transverse axis T-T) and prevents skewing of member 40 as it translates in the axial direction L-L.

The main body 48 is substantially ring-shaped, as shown in FIGS. 2A-2B, with the perimeter thereof forming an oblong circle corresponding to the oblong circular shape of opening 12, such that at least portions of opposing sides 48S are angled with respect to one another, such that the distance between sides 48S nearer the slotted end 49 is less that the distance between sides 48S nearer the opposite end, with the maximum distance 46 being shown in FIG. 2B. At least portions of opposing ends 48E are curved, as shown in FIG. 2B. Additionally, main body 48 is formed as a split ring such that one end 48E is provided with a wedge-shaped gap 49. In one example, gap 49 is about 1.2 mm wide at the bottom (narrowest width) of the gap, although this width may vary and be lesser or greater than 1.2 mm by about 0.75 mm. In one thin member embodiment, 49 is about 1.2 mm at the bottom of the wedge and opens with an angle of about twenty degrees to the top. The width at the top of the wedge is about 1.819mm.

An extension 50 is provided on each side 48S of ring 40. The extensions 50 extend in the transverse direction from the flat side portions 48S, respectively, as shown in FIG. 2B. Extensions 50 are configured and dimensioned to be received in slots 26 (e.g., see FIG. 1A), that are provided in the side walls 12S, respectively. Slots 26 open at ends that open to the inner surfaces of the side wall 12S, to receive extensions 50. However, the opposite ends of the slots 26 are closed to the outer surfaces of side walls 12S. Extensions 50 have a convex contact surface 52, with the greatest distance from the side surface 48S being about in the middle of the contact surface. This distance (width dimension) 54 is about 0.575 mm±0.25 mm and the dimension 25 is about 0.65 mm±0.25 mm. Preferred tolerance between 48S and 12S is about ±0.1 mm, more preferably about ±0.03 mm. The closed end 25 of the slot (at the bottom depth of) 24 is curved similar to the curvature of 52. Accordingly, the slot 26 forms a curved surface with a maximum distance 25 into the side 12S. The length/height 26L (see FIG. 1A) of slot 26 is greater than the length/height 55 (see FIG. 2E) of extension 50. This allows extensions 50 to axially slide in slots 26 in directions along the longitudinal axis L-L. Height 55 of an extension 50 may be a dimension within the range of from about 1.55 mm to about 2.7 mm, typically from about 2.05 mm to about 2.2 mm. The dimension of 26L may range, for example from about 2.1 mm to about 3.1 mm, and, in at least one embodiment, is preferably about 2.6 mm.

Figure 2C:
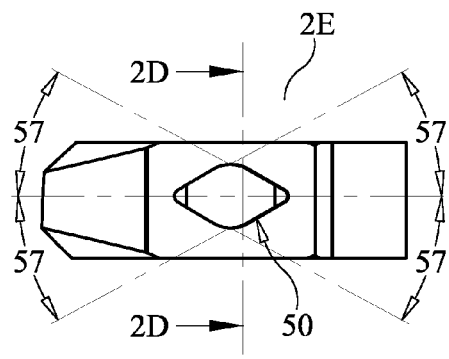
FIG. 2C is a side view of the member of FIG. 2A.
Figure 2D:
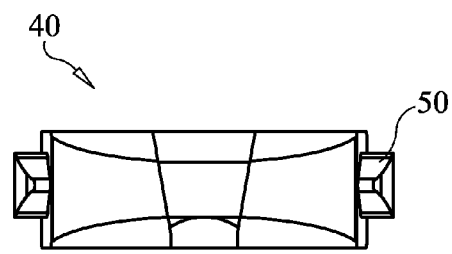
FIG. 2D is an end (side) view taken from the left in FIG. 2B.
Figure 2E:
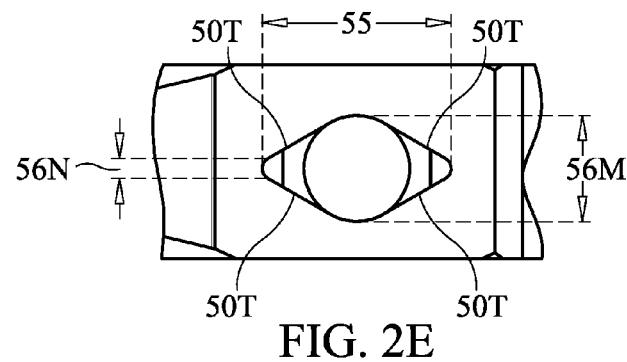
FIG. 2E is a detail view taken from circle 2E in FIG. 2C.

The thickness of extension 50 varies from a maximum thickness 56M of an intermediate portion thereof to a minimum thickness 56N at top and bottom ends of member 50, see FIG. 2E. Thickness 56M is only slightly less than thickness 27 (see FIG. 1D) of slot 24. This provides a certain amount of tolerance to allow extension 50 to axially slide in slot 24, while minimizing axial translation in the thickness direction, and maintaining a secure connection of member 40 within the plate 10. The dimension 56M may range from about 0.95 mm to about 1.55 mm, typically from about 1.15 mm to about 1.35 mm. The dimension 56N is about 0.2 mm to about 0.3 mm. The dimension of 27 is in the ranged of about 1.25mm to about 1.35 mm. The tolerance between 56M and 27 forms a gap of about 0.0095 mm to about 0.15 mm, more preferably about 0.098 mm to about 0.13 mm. Extensions 50 are tapered in the thickness dimension, from the maximum thickness 50M at the intermediate location, to the minimum thicknesses 50N at the top and bottom ends of extension 50 as shown in FIGS. 2C and 2E. The tapered surfaces 50T of extension 50 allow the extension 50 and thus the member 40 to rotate about the transverse axis T-T relative to plate 10. Surfaces 50T taper linearly from thickness 50M to thickness 50N as shown in FIG. 2E. An angle 57 (see FIG. 2C) formed by one of tapered surfaces 50T relative to a line 58 connecting the top and bottom ends and passing through the center, in the thickness dimension of extension 50, as shown in FIG. 2C is in the range of about twenty-five degrees to about forty-five degrees, typically about thirty degrees. Accordingly, this provides a dynamic fixator interface member 40 installed in opening 12 with the ability to rotate up to about forty-five degrees (typically about thirty degrees) relative to plate 10 in each of opposite directions about the transverse axis T-T.

Dynamic fixator interface member 40 is thither provided with an anti-backout mechanism 60 (see FIG. 2A) configured and dimensioned to prevent backout of a fastener 70, 70' therefrom, once the fastener 70, 70' has been inserted through the dynamic fixator member 40 and fastened to the spinal column 1, for example. When the fastener 70, 70' is inserted through the member 40, the tapered part of the head of the fastener 70, 70' expands the member 40 (enabled by the slot 49) until the shoulder (e.g., distal end) of the head passes the shoulder 60 on member 40. The member 40 then recoils to its original, non-expanded configuration such that shoulder 60 overlies the shoulder of the fastener 70, 70'. The shoulder 60 thus prevents the fastener from backing out of the member 40 unless the member 40 is intentionally forced into an expanded configuration, such as by inserting a tool in gap 49 to wedge it apart. In the embodiment shown in FIG. 2A, anti-backout mechanism 60 comprises an extension or shoulder extending inwardly from the main body 48 of member 40.

Figure 3A:
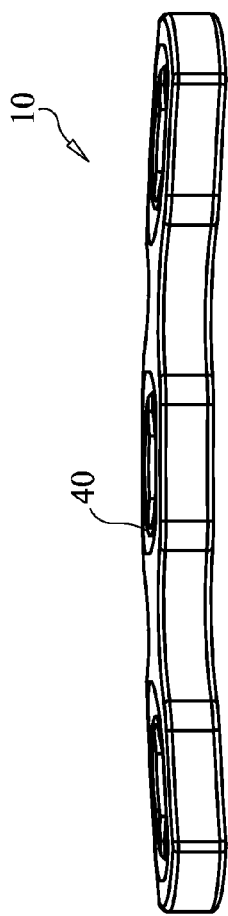
FIGS. 3A-3B show a side view and a top view, respectively, of a plate after installation of dynamic fixator interface members into fixator receptor openings according to an embodiment of the present invention.
Figure 3B:
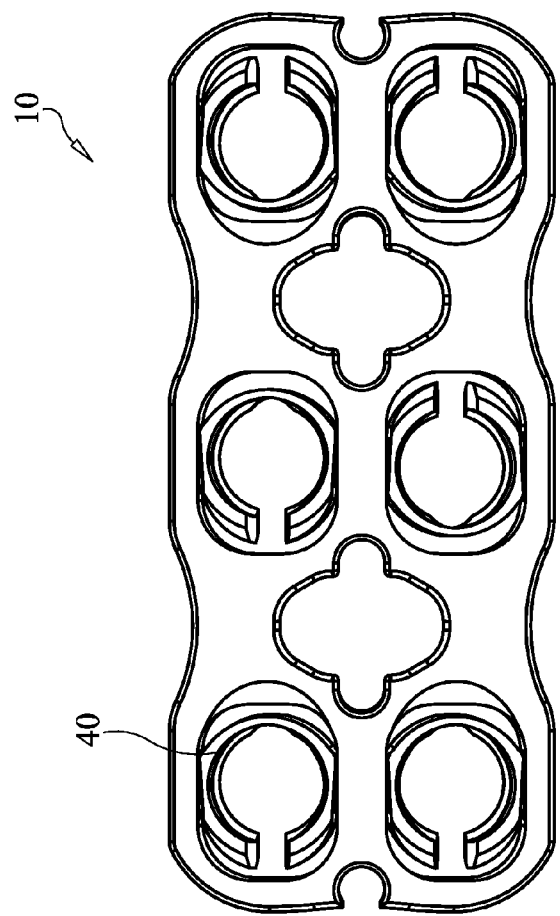
Figure 5A:
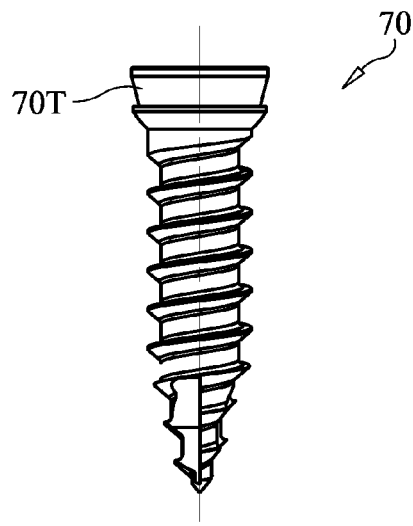
FIGS. 5A-5B show a side view and a top view of a fixed fastener according to an embodiment of the present invention.
Figure 6A:
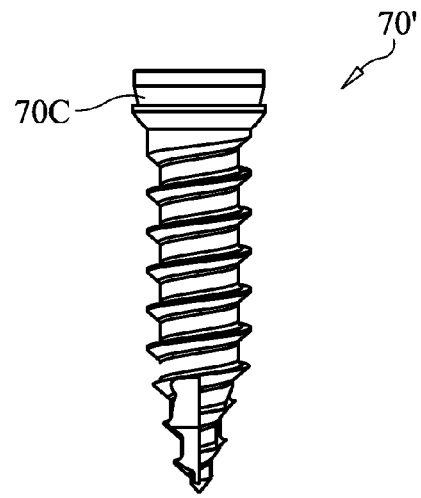
FIGS. 6A-6B show a side view and a top view of a variable fastener according to an embodiment of the present invention.
Figure 5B:
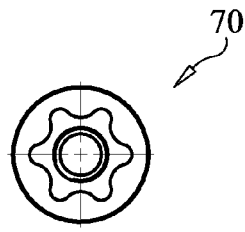
Figure 6B:

FIGS. 3A-3B show a side view and a top view, respectively, of plate 10 after installation of dynamic fixator interface members 40 into fixator receptor openings 12. To install a fixator interface member 40 into a fixator receptor opening 12, the main body 48 is squeezed so as to flex the opposite portions adjacent gap 49, thereby temporarily reducing the width of the gap 49. This also temporarily reduces the overall width (54 plus 46 plus 54) of member 40, thereby allowing extensions 50 to be more easily fitted into slots 24. Once extensions 50 have been received in slots 24, the squeezing force on the main body 48 can be released, whereby the main body resiliently returns to its original shape and dimensions, pre-squeezing. Such as shown in FIG. 2B. Thus, the member 40 returns to its original width whereby extensions 50 are securely retained within slots 24 (while still allowing axial translation and rotation, as described above. The orientations of the slots/gaps 49 (e.g., up for the top members 40, down for the inferior members 40 and one up, one down for the intermediate members in FIG. 3B) are orient to provide easy access to and visualization of the slots if removal of a fastener 70, 70' is desired, based on common fastener placements and angulation relative to the plate 10 during an implantation.

Figure 7:
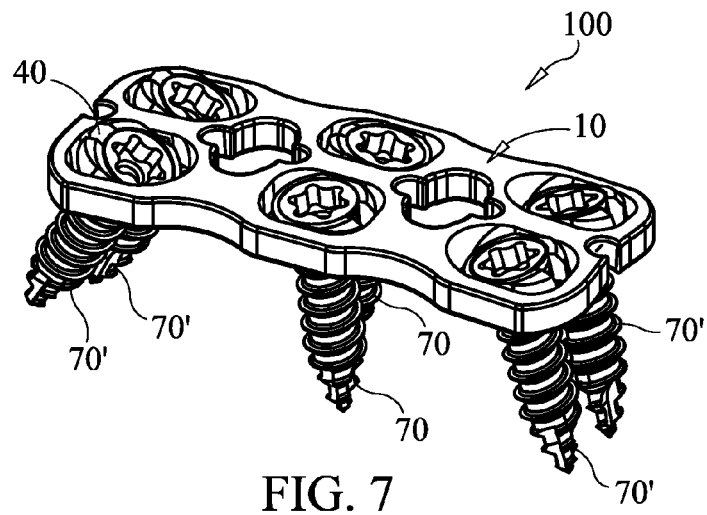
FIG. 7 illustrates a system in which members have been installed in a plate and fasteners have been installed in the members according to an embodiment of the present invention.

Once dynamic fixator interface members 40 have been installed in openings 12 of plate 10, as described above, then fasteners 70, 70' can be installed in fixator interface members 40. FIG. 7 illustrates a system 100 in which members 40 have been installed in plate 10 and fasteners 70, 70' have been installed in members 40. In the embodiment shown in FIG. 7, fixed screws 70 have been installed in the intermediate members 40, while variable screws 70' have been installed in the members 40 of the top end portion and members 40 of the bottom end portion. Once the variable screw 70' is locked (i.e., engaged with the anti-backout mechanism 60 of member 40), member 40 can still rotate and translate. Fixed screw 70 does not angulate relative to member 40 either, after complete installation of screw 70 into member 40. There is no angulation between the member 40 and the fixed 70 or variable 70' screws, which angulate only to the amount of angulation ability of member 40 relative to plate 10. Thus, both screws 70 and 70' have the same angle range, which is the range of the angulation ability of the member 40 relative to the plate 10.

The fixed screw 70 has a tapered head 70T upper part (above the shoulder of the antibackout mechanism), whereas the variable screw 70' has a cylindrical head 70C upper part (above the shoulder of the antibackout mechanism). The cylindrical head 70C of the variable screw 70' lets the member 40 recoil to is original (unexpanded/relaxed) shape and thus, allow the same motion of the member 40 with the screw 70' locked inside relative to the plate 10, i.e., it creates a non-constrained interface. In contrast, the tapered head 70T of the fixed screw 70 expands the member 40 to create friction between the flats 48s of the member 40 and the flats 12s of the plate 10, thus maintaining the angle of the member 40 (with the screw 70 inside) relative to the plate 10, i.e., it creates a constrained interface.

Figure 8:
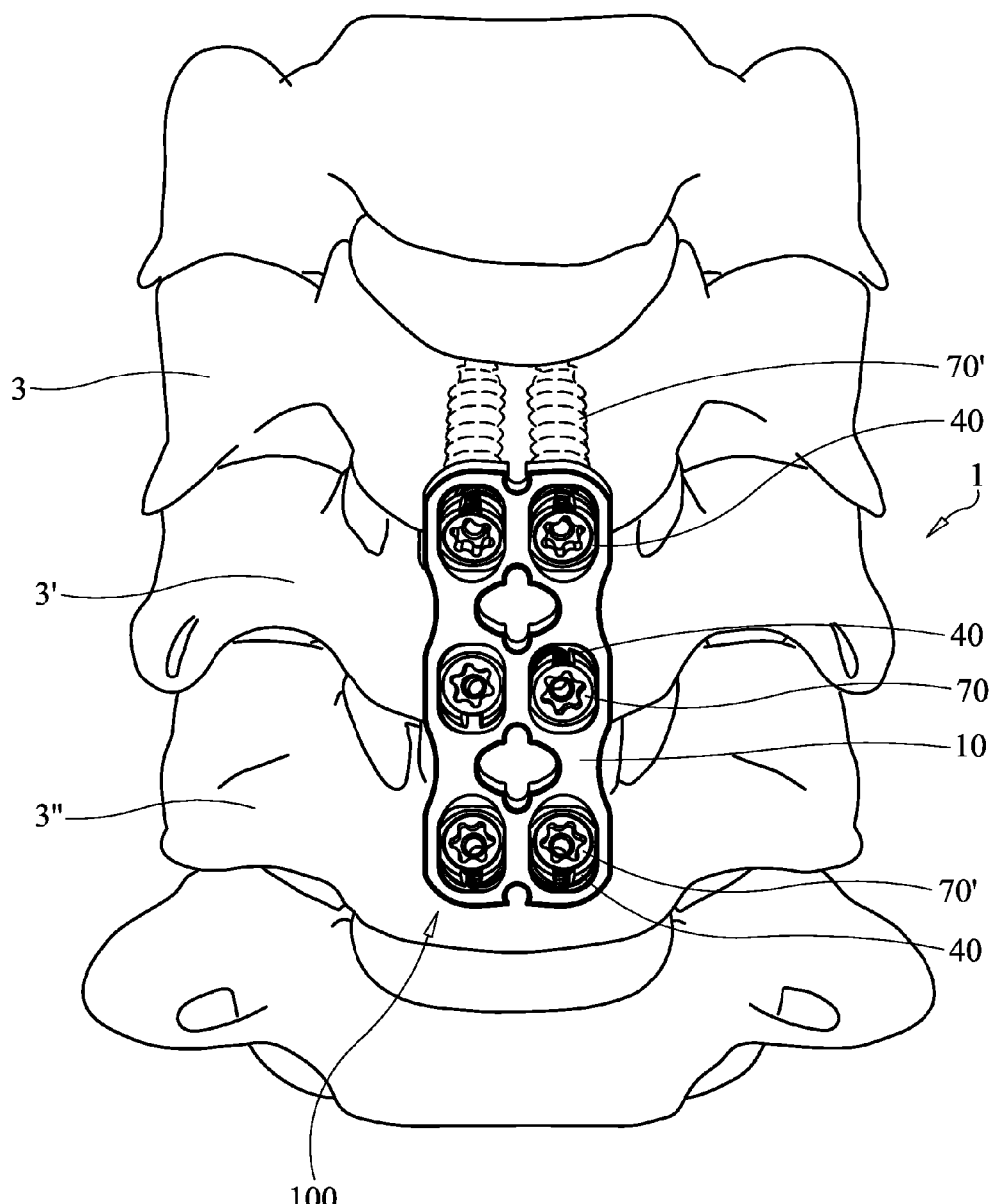
FIG. 8 illustrates a system according to an embodiment of the present invention having been attached to the spinal column of a patient.

FIG. 8 illustrates system 100 having been attached to the spinal column 1 of a patient. Specifically, FIG. 8 shows system 100 having been attached to the anteriorly to vertebrae 3, 3' and 3". To perform this attachment/implantation, fasteners (e.g., variable screws) 70' passing through the members 40 in the top portion of plate 10 are angulated so that the pointed distal ends of the fasteners 70' are angled upwardly, like illustrated in FIG. 7, fasteners (e.g., fixed screws) 70 passing through the middle members 40 in plate 10 are oriented perpendicular relative to the face of plate 10 (also like shown in FIG. 7) and fasteners (e.g., variable screws) 70' passing through the members 40 in the bottom portion of plate 10 are angulated so that the pointed distal ends of the fasteners 70' are angled downwardly, (also like illustrated in FIG. 7). The fasteners 70' in the top portion are attached (e.g., screwed into) vertebra 3 along upwardly angled pathways corresponding to the upward orientations of the fasteners 70' of the top portion. Fasteners 70 in the middle portion are attached (e.g., screwed into) vertebra 3' along generally horizontal (i.e., perpendicular to the face of plate 10, substantially horizontal when the patient is standing) pathways corresponding to the perpendicular orientations of the fasteners 70 of the middle portion. Fasteners 70' in the bottom portion are attached (e.g., screwed into) vertebra 3" along downwardly angled pathways corresponding to the downward orientations of the fasteners 70' of the bottom portion of plate 10.

Once system 100 is attached as shown in FIG. 8 and described above, the patient can be closed according to known techniques to complete the implantation process. Once the patient has recovered to the extent where the patient can at least sit upright, the gravitational forces on the spine 1 typically cause some subsidence forces to be applied to the treated vertebrae 3, 3',3" particularly in cases where one or more grafts have been placed between one or more pairs of adjacent vertebrae. System 100 allows this subsidence to occur, thereby maintaining optimum contact and pressure on any grafts that may have been placed to maximize the chances for successful union. The ability of members 40 to slide axially, when variable screws 70' are used, relative to plate 10 allows the subsidence to occur without untoward resistance toward the subsidence movements. Likewise, the ability of the members 40, along with variable fixators 70', to rotate prevents binding of the fixators 70' so that they do not resist the subsidence movements.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A system for fixation to a spinal column, said system comprising: a plate having an anterior surface, a posterior surface, a longitudinal axis, a transverse axis normal to said longitudinal axis and a through hole passing through said anterior and posterior surfaces, said through hole shaped as an oblong circle in said anterior surface of said plate, the oblong circle having a major diameter oriented along the longitudinal axis of said plate, and having opposing sides parallel to one another; a dynamic fixator interface member configured and dimensioned to connect to said plate within said through hole and to axially slide in translation relative to said plate in a direction along said longitudinal axis, and additionally, to rotate relative to said plate in directions about said transverse axis; wherein said dynamic fixator interface member comprises a ring-shaped body having a gap in its perimeter, thereby allowing said ring-shaped body to be compressed for insertion into said through hole, as well as to be expanded to lock flat sides of said ring-shaped body against said opposing walls of said through hole to prevent rotation of said dynamic fixator interface member relative to said plate; a variable fastener having a head configured to be received in an opening of said ring-shaped body such that, after receiving said head of said variable fastener, said ring-shaped body resumes an original, unexpanded configuration and can rotate relative to said plate; and a fixed fastener having a head configured to be received in said opening of said ring-shaped body such that, after receiving said head of said fixed fastener, said ring-shaped body is expanded to contact said flat sides against said opposing sides of said through hole, thereby preventing rotation of said dynamic fixator interface member relative to said plate.

2. The system of claim 1, further comprising slots in opposite inner walls defining opposing sides defining through hole, wherein said dynamic fixator interface member axially slides in said slots.

3. The system of claim 2, wherein said dynamic fixator interface member comprises first and second extensions extending from flat sides of said ring-shaped body, wherein said first and second extensions slide in said slots.

4. The system of claim 3, wherein said first and second extensions are configured to rotate in first and second directions in said slots, relative to said transverse axis of said plate.

5. The system of claim 3, wherein said first and second extensions each comprise tapered surfaces, a first end, a second end and an intermediate location, wherein each said intermediate location has a first thickness, and each of said first and second ends have a second thickness, said first thickness being greater than said second thickness, and wherein said tapered surfaces of said extensions taper linearly from said intermediate location to said first and second ends, respectively, for each of said first and second extensions.

6. The system of claim 5, wherein an angle formed by one of said tapered surfaces relative to a line connecting said first and second ends of one of said first and second extensions is in the range of twenty-five degrees to forty-five degrees.

7. The system of claim 6, wherein said angle is thirty degrees.

8. The system of claim 2, wherein said slots are positioned in alignment parallel to said longitudinal axis.

9. The system of claim 1, wherein said dynamic fixator interface member is configured to rotate up to forty-five degrees relative to said plate in directions about said transverse axis.

10. The system of claim 1, wherein said dynamic fixator interface member is configured to rotate not greater than thirty degrees relative to said plate in directions about said transverse axis.

11. The system of claim 1, wherein said dynamic fixator interface member further comprises an anti-backout mechanism configured to prevent backout of a fastener therefrom, once the fastener has been inserted through the dynamic fixator interface member and fastened to the spinal column, said dynamic fixator interface member having been located in said through hole.

12. The system of claim 11, wherein said anti-backout mechanism comprises an extension extending from said body.

13. The system of claim 1, wherein said fixed fastener comprises a fixed screw and said head of said fixed screw comprises a tapered head that increases in size toward a proximal end of said head.

14. The system of claim 1, wherein said variable fastener comprises a variable screw and said head of said variable screw is cylindrical.

15. The system of claim 1, comprising:
   at least two of said dynamic fixator interface members; and
   at least two of said through holes comprising closed-ended slots formed in opposite inner walls of each of said at least two through holes, said closed-ended slots configured and dimensioned to connect with said at least two dynamic fixator interface members, respectively and to allow subsidence of vertebrae of the spinal column that said plate system is adapted to be fixed to.

16. A plate system for fixation to a spinal column, said plate system comprising:
   a plate having an anterior surface, a posterior surface, a longitudinal axis, a transverse axis normal to said longitudinal axis and a plurality of through holes passing through said anterior and posterior surfaces, said through holes having a length and a width, said length being greater than said width, and wherein side walls of said through holes extend parallel to one another and to said longitudinal axis and define sides of said through holes from said anterior surface to said posterior surface, wherein each through hole of said plate is configured to receive a dynamic fixator interface member, wherein said dynamic fixator interface member comprises a ring-shaped body having a gap in its perimeter, thereby allowing said ring-shaped body to be compressed for insertion into said through hole, as well as to be expanded to lock flat sides of said ring-shaped body against said opposing walls of said through hole to prevent rotation of said dynamic fixator interface member relative to said plate; a variable fastener having a head configured to be received in an opening of said ring-shaped body such that, after receiving said head of said variable fastener, said ring-shaped body resumes an original, unexpanded configuration and can rotate relative to said plate; and a fixed fastener having a head configured to be received in said opening of said ring-shaped body such that, after receiving said head of said fixed fastener, said ring-shaped body is expanded to contact said flat sides against said opposing sides of said through hole, thereby preventing rotation of said dynamic fixator interface member relative to said plate;

at least one viewing opening located between at least two of said through holes along a direction of said longitudinal axis, said at least one viewing opening being configured to allow viewing of a graft or cage inserted between adjacent vertebrae when said plate is implanted to the vertebrae; and at least two of said through holes comprising closed-ended slots formed in said side walls of each of said at least two through holes, said closed-ended slots configured and dimensioned to allow translation of received therein, in directions that said longitudinal axis.

17. The system of claim 16, wherein one of said dynamic fixator interface members is received in said slots of each said through hole having said slots, respectively, each said dynamic fixator interface member being configured and dimensioned to slide in the respective slots of said through hole it is received in, wherein sliding is permitted axially relative to said plate in directions of said longitudinal axis.

18. The system of claim 17, wherein each said dynamic fixator interface member is configured and dimensioned to rotate in said slots, relative to said plate, in directions about said transverse axis.

19. The system of claim 16, wherein one of said dynamic fixator interface members is received in said slots of each said through hole having said slots, respectively, each said dynamic fixator interface member being configured and dimensioned to rotate in the respective slots of said through hole it is received in, wherein rotating is permitted relative to said plate in directions about said transverse axis.

20. A plate system for fixation to a spinal column, said system comprising:

a plate having an anterior surface, a posterior surface, a longitudinal axis, a transverse axis normal to said longitudinal axis and a plurality of through holes passing through said anterior and posterior surfaces, the through holes having a length and a width, said length being greater than said width;

a plurality of dynamic fixator interface members, one of each members received in one of each said through holes, respectively, each said dynamic fixator interface member being configured and dimensioned to connect to said plate within said respective through hole and to axially slide in translation relative to said plate in a direction along the longitudinal axis, and additionally, to rotate so as to form an angle relative to said anterior surface of said plate wherein each dynamic fixator interface member comprises a ring-shaped body having a gap in its perimeter, thereby allowing said ring-shaped body to be compressed for insertion into said through hole, as well as to be expanded to lock flat sides of said ring-shaped body against said opposing walls of said through hole to prevent rotation of said dynamic fixator interface member relative to said plate;

a variable fastener having a head configured to be received in an opening of one of said dynamic fixator interface members such that, after receiving said head of said variable fastener, said dynamic fixator interface member resumes an original, unexpanded configuration and can rotate relative to said plate; and a fixed fastener having a head configured to be received in said opening of one of said dynamic fixator interface members such that, after receiving said head of said fixed fastener, said dynamic fixator interface member is expanded to contact said sides of said dynamic fixator interface member against opposing sides of said through hole, thereby preventing rotation of said dynamic fixator interface member relative to said plate.

21. The system of claim 20, wherein said opposing sides extend parallel to each other and parallel to said longitudinal axis.

* * * * *